United States Patent [19]
Lohr et al.

[11] Patent Number: 6,022,722
[45] Date of Patent: Feb. 8, 2000

[54] RENATURATION OF PROTEINS

[75] Inventors: Frauke Lohr, Recklinghausen; Andreas Pawlik, Vechelde; Hubert Motschmann; Martina Bree, both of Berlin; Euridice Vieira, Guimaraes; Alexander Welle, Ladenburg, all of Germany

[73] Assignee: Huels Aktiengesellschaft, Marl, Germany

[21] Appl. No.: 09/088,058

[22] Filed: Jun. 1, 1998

[30] Foreign Application Priority Data

May 31, 1997 [DE] Germany .......................... 197 22 950

[51] Int. Cl.[7] .............................. C07K 1/02; C07K 1/04
[52] U.S. Cl. ........................ 435/199; 435/206; 435/213; 435/222; 530/352; 530/356; 530/357; 530/358; 530/359; 530/364; 530/369; 530/382; 530/385; 530/386; 530/400; 530/427
[58] Field of Search ..................... 530/350, 395, 530/356, 357, 352, 359, 358, 364, 366, 368, 369, 382, 385, 386, 400, 424, 427; 435/183, 188, 199, 206, 213, 222

[56] References Cited

U.S. PATENT DOCUMENTS 4,885,164  12/1989  Thurow ................................. 424/85.4

FOREIGN PATENT DOCUMENTS 197 17 431  10/1998  Germany .

OTHER PUBLICATIONS

Galat et al. Reversed Unfolding–Refolding Process . . . , Biochemistry, vol. 20, pp. 7415–7423, 1981

Goto et al, Mechanism of Acid–Induced Folding of Proteins. Biochemistry. vol. 29, pp. 3480–3488, 1990.

Lu et al. Folding of a Partially Folded State . . . FASEB Journal, vol. 9, No. 6, p. A1242, Abstract No. P22, Apr. 24, 1995.

Arthur Cammers–Goodwin, et al., J. Am. Chem. Soc., vol. 118, pp. 3082 to 3090, "Mechanism of Stabilization of Helical Conformations of Polypeptides by Water Containing Trifloroethanol", 1996.

F. D. Sönnichsen, et al., Biochemistry, vol. 31, pp. 8790 to 8798, "Effect of Trifluoroethanol on Protein Secondary Structure: An NMR and CD Study Using a Synthetic Actin Peptide", 1992.

Jeffrey S. Albert, et al., Biochemistry, vol. 34, pp. 984 to 990, "Stabilization of Helical Domains in Short Peptides Using Hydrophobic Interactions", 1995.

A. I. Arukumar, et al., Biochimica et Biophysica Acta, vol. 1338, pp. 69 to 76, "Non–Specific Helix–Induction in Charged Homopolypeptides by Alcohols", 1997.

Yee–Hsiung Chen, et al., Biochemistry, vol. 11, No. 22, pp. 4120 to 4131, "Determination of the Secondary Structures of Proteins by Circular Dichroism and Optical Rotatory Dispersion", 1972.

Carl R. McMillin, et al., Journal of Colloid and Interface Science, vol. 48, No. 2, pp. 345 to 349, "A Circular Dichroism Technique for the Study of Adsorbed Protein Structure", Aug. 1974.

Linda J. Smith, et al., Biochimica et Biophysica Acta, vol. 1121, pp. 111 to 118, "Measurement of the Secondary Structure of Adsorbed Protein by Circular Dichroism. 1. Measurements of the Helix Content of Adsorbed melittin", 1992.

W. Norde, et al., Journal of Colloid and Interface Science, vol. 112, No. 2, pp. 447 to 456, "Protein Adsorption at Solid–Liquid Interfaces: Reversibility and Conformation Aspects", Aug. 1986.

(List continued on next page.)

Primary Examiner—Jeffrey E. Russel
Attorney, Agent, or Firm—Oblon, Spivak, McClelland, Maier & Neustadt, P.C.

[57] ABSTRACT

The invention relates to a method for the renaturation of denatured proteins in which they are treated with a renaturant which has on vicinal carbon atoms a hydroxyl group and at least one fluorine atom.

16 Claims, 1 Drawing Sheet

OTHER PUBLICATIONS

Willem Norde, et al., Colloids and Surfaces, vol. 64, pp. 87 to 93, "Structure of Adsorbed and Desorbed Proteins", 1992.

Chemical Abstracts, vol. 123, No. 23, Dec. 4, 1995, AN 308838, G.D. Fasman, "Confromation of Membrane Proteins: Bacteriorhodopsin", from Gov. Rep. Announce. Index, Abstract No. 456730, vol. 94, No. 20, 1994.

File Medline, AN 93–364269, 1993, G. Sirokman, et al., "Refolding and Proton–Pumping Activity of a Polyetheylene Glucol–Bacteriorhodopsin Water–Soluble Conjugate", vol. 2, No. 7, Jul. 1993.

RENATURATION OF PROTEINS

BACKGROUND OF THE INVENTION

1. Field of the Invention

The present invention relates to a method for the renaturation of denatured proteins by treatment with a renaturant.

2. Description of the Related Art

A wide variety of types of proteins which occur in plant and animal organisms and have various types of effects on the structure, the function and the metabolism of the cells are prone to lose, under various influences, their natural three-dimensional folding pattern, which is called the secondary structure, and to become denatured. The denaturation includes breakdown of the intramolecular interaction, especially hydrogen bonds, and thus loss of the α-helix structure which virtually all native proteins have, at least in parts of the molecule, and which, as part of the secondary structure, is decisively responsible for the activity of the protein.

One of the influences leading to denaturation is heating to a temperature which may be up to 150° C., depending on the protein. Other influences of this type are changes in the pH to below 3 or above 9, addition of denaturing reagents such as urea, guanidine or amide solutions, introduction into foaming solutions, spreading on surfaces, irradiation with UV or X-rays or use of wetting agents.

It is not uncommon in industry for proteins to be unintentionally but unavoidably denatured because their environment is, for other reasons, subjected to conditions under which denaturation takes place. One example thereof is steam sterilization of biomaterials, in which proteins immobilized thereon are denatured. Another example is UV irradiation of polymer surfaces with proteins adsorbed or immobilized thereon to prepare for grafting with monomers intended to modify the surface properties. Valuable proteins such as blood proteins may furthermore undergo unwanted denaturation, for example by the pH getting into the dangerous range on binding to and modification of surfaces.

It is known that trifluoroethanol preserves the secondary and tertiary structure of proteins (F. D. Sönnichsen et al., Biochemistry 1992, 31, 8790–8798; J. S. Albart et al., Biochemistry 1995, 34, 984–990; A. Cammers-Goodwin et al., J. Am. Chem. Soc. 1996, 118, 3082–2890) and, furthermore, induces non-specific helical foldings, so that the resulting proteins have different dominant folding patterns and are thereby denatured (A. J. Arunkumar et al., Biochimica et Biophysica Acta 1997, 1338, 69–79).

SUMMARY OF THE INVENTION

It would therefore be desirable to have available a method which can be used for the renaturation of denatured proteins. It has now been found that denatured proteins are at least partially renatured when they are treated with a renaturant which has on vicinal carbon atoms a hydroxyl group and at least one fluorine atom (the phrase "vicinal carbon atoms" refers to two carbon atoms which are adjacent to each other). Surprisingly, denatured proteins in fact redevelop their natural secondary structure so that their biological function is restored when they are treated with one of the renaturants of the present invention. In this case there is at least partial reformation of the α-helix. The extent of the renaturation which can be achieved varies from protein to protein. Very substantial renaturation is achieved under favorable conditions.

Each denatured protein capable of being renatured by the method of the present invention is completely denatured (i.e, the denatured protein has lost all of the hydrogen bonding present in the native protein before denaturation), or is partially denatured (i.e., the denatured protein has lost some degree of the hydrogen bonding present in the native protein before denaturation). Each denatured protein renatured by the method of the present invention is completely renatured (i.e, the renatured protein has the conformation of the native protein before denaturation) or is partially renatured (i.e., the renatured protein regains at least some degree of the hydrogen bonding present in the native protein before denaturation). Denatured proteins renatured by the method of the present invention show the same functionality as before the denaturation. Preferably, the partially renatured protein regains at least 5% of the hydrogen bonding present in the native protein before denaturation (i.e., the renatured protein is at least 5% renatured). More preferably, the partially renatured protein regains at least 50% of the hydrogen bonding present in the native protein before denaturation (i.e., the renatured protein is at least 50% renatured). Most preferably, the partially renatured protein regains at least 95% of the hydrogen bonding present in the native protein before denaturation (i.e., the renatured protein is at least 95% renatured).

BRIEF DESCRIPTION OF THE DRAWINGS

FIG. 1) and human fibrinogen (HFb; FIG. 2) in the native and denatured state and the state renatured according to the invention; it is evident that the curves for the denatured proteins differ considerably from the curves for the originally native proteins, while the curves for the renatured proteins substantially correspond once again to those for the native proteins.

DETAILED DESCRIPTION OF THE PREFERRED EMBODIMENTS

Figure 1:
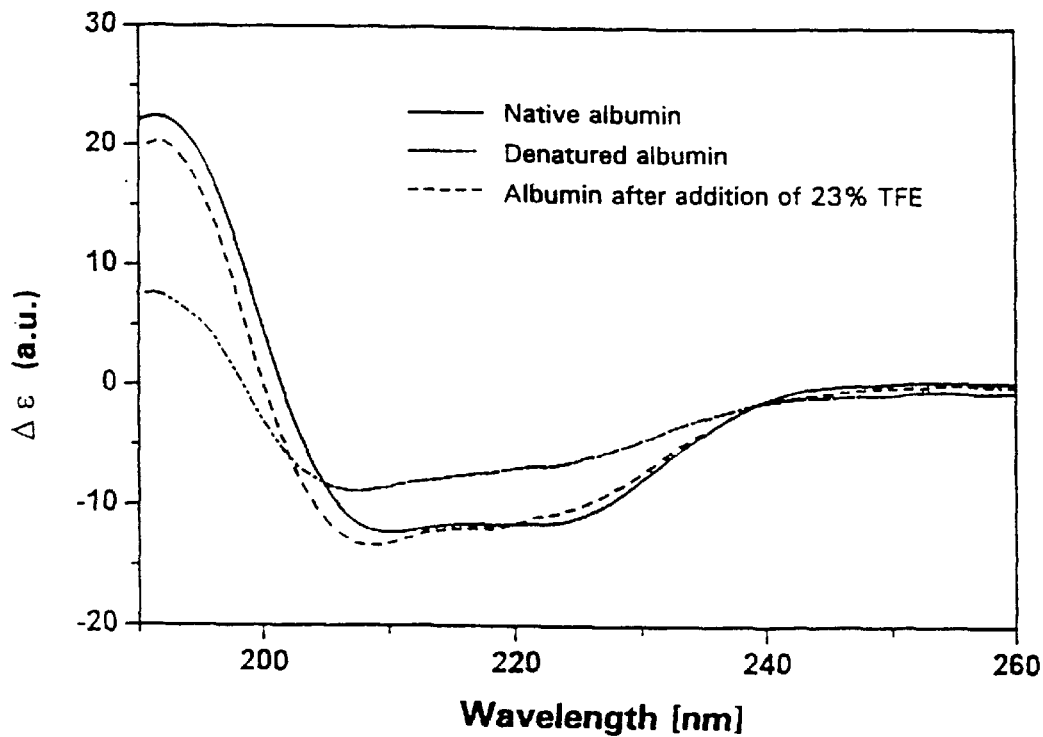
FIGS. 1 and 2 show the circular dichroism (CD) spectra of human serum albumin (HSA.

Denatured proteins for the purpose of this invention are those which, according to an analysis by CD spectroscopy (explained hereinafter), no longer have their original structure consisting of α-helix, β-pleated sheet and other features. Proteins which may be mentioned as examples of those which can be renatured by the method of the invention are: albumins, fibrinogen, apolipoproteins, lysozymes, subtilisin, ribonucleases, myoglobins, trypsins, chymotrypsin, cytochrome C, calmodulin, melittin, protein C, globulins, histones, prolamins, protamines, keratins and collagen.

The most effective renaturants are those which contain 3 fluorine atoms on a carbon atom which is adjacent to a carbon atom with a hydroxyl group, that is to say have a trifluoromethyl group. Apart from the functional groups mentioned, the renaturants may have a hydrocarbon structure or have additional groups or atoms which do not interfere with the purpose of use, such as carboxylic ester groups, ether linkages or halogen atoms. Since the renaturation advantageously takes place in aqueous medium, the renaturants should be at least slightly soluble in water, for example up to 1% by weight in water at 20° C. The solubility in water can, where appropriate, be increased by additional hydrophilic groups (besides the mentioned hydroxyl group on one of the vicinal carbon atoms). Thus, the renaturants may contain, for example, further hydroxyl groups.

Suitable renaturants which may be mentioned are: monofluoroethanol, difluoroethanol and, in particular, trifluoroethanol;1-fluoro-2-propanol, 1,1-difluoro-2-propanol, 1,1,1-trifluoro-2-propanol, 1,1,1,3-tetrafluoro-2-propanol, 1-trifluoromethyl-1,1-hexanediol and hexafluoroisopropanol.

The method of the invention is carried out by allowing the renaturant to act in an aqueous medium on dissolved, suspended or adsorbed denatured proteins, in particular at a temperature which is expediently from 0° C. to 60° C. The concentration of the renaturant can vary within wide limits and be, for example, from 0.5 to 95% by volume based on the renaturation mixture consisting of the aqueous medium with the denatured protein and the renaturant. The renaturation generally takes from 5 to 60 minutes.

An indication of the renaturation is obtained by circular dichroism (CD) spectroscopy, which can be used to elucidate the absolute conformation of chiral (or optically active) compounds and to follow changes in conformation. This entails linearly polarized light, generally in the visible or UV region, being passed through the chiral compound which is, for example, present in solution or adsorbed on a transparent medium. If the incident wavelength is in the region of absorption by the chiral compound, electronic transitions may occur, leading to an elliptical polarization of the previously linearly polarized light, which can be regarded as superimposition of one constituent wave circularly polarized to the right and one circularly polarized to the left, with equal amplitudes. The absorption coefficients of a chiral compound for the constituent waves circularly polarized to the right and to the left are not necessarily identical. The difference in the molar decadic absorption coefficients for the constituent wave circularly polarized to the left and that circularly polarized to the right is referred to as circular dichroism. After passing through the sample, the parts of the original constituent waves which remain after absorption become superimposed and result in an elliptically polarized light because, in general, they no longer have the same amplitude. Alteration of the wavelength of the incident light results in a spectrum which shows the circular dichroism as a function of the wavelength.

It is likewise possible to pass right- and left-polarized light successively through the sample to result in a difference spectrum which provides information on the structure of the chiral compound, and about its absolute conformation. The chiral compounds investigated by CD spectroscopy include various proteins. Changes in the conformation of proteins at interfaces have also been investigated by CD spectroscopy (see, for example, Y. H. Chen et al., Biochemistry, Vol. 11, No. 22 (1972), 4120–4131; C. R. MacMillin et al., Journal of Colloid and Interface Science 48, No. 2, (1974) 345–349; L. J. Smith et al., Biochimica et Biophysica Acta, 1121 (1992) 111–118; W. Norde et al., Journal of Colloid and Interface Science, 112, No. 2, 447–456; W. Norde et al., Colloids and Surfaces 62 (1992), 87–93).

If the proteins are dissolved or adsorbed on substrates transparent to light of the relevant wavelength it is possible to carry out transmission measurements. However, this is impossible on adsorption onto opaque substrates, for which reflection measurements are available. However, the precondition for this is that a sufficiently strongly reflecting surface is present, which is often not the case. An elegant method for obtaining CD spectra of adsorbed proteins (and other chiral compounds) by reflection measurement is described in German Patent Application 197 17 431.0.

For information on renaturation, a native protein with intact secondary structure can be dissolved or adsorbed on a substrate and its CD spectrum can be recorded. The protein is then denatured, for example by heating, and the CD spectrum of the denatured protein is recorded and differs markedly from that of the native protein. The renaturant is then added. Recording of the CD spectrum reveals agreement with the spectrum recorded before the denaturation if the original secondary structures have been reformed.

One method for demonstrating renaturation of proteins and the extent of renaturation is the assay method called ELISA (Enzyme Linked Immuno Sorbent Assay). The basis for this assay is the specific reaction of antibodies with antigens, which may be, for example, blood proteins. The specificity or the binding affinity of such an antigen-antibody binding moreover depends greatly on the structure of the antigen. The term used in this connection is the lock and key principle. High-affinity binding between antibody and antigen occurs only if a particular structure, for example a domain, of the antigen (key) fits the molecular structure of a particular antibody region (lock). If, in contrast to native proteins, the specific binding site is destroyed by denaturation, the antibody is no longer able to bind. Renaturation of a protein can therefore be demonstrated by detectability of a reaction in the ELISA with the antibody, which did not occur in the previous assays.

One variant of the demonstration is to carry out an indirect ELISA. In this case, the antigen is adsorbed onto a solid phase in a first step. In the second step, a primary antibody is bound to the adsorbed antigen. In a third step there is addition of another, so-called secondary, antibody which has specific binding sites for the primary antibody which thus in turn acts as antigen. This secondary antibody is conjugated to an enzyme. In a fourth step, the antigen antibody complex is reacted with a substrate solution. Reaction of the attached enzyme with the substrate present in the solution initiates a color reaction whose optical density is proportional to the amount of bound antigen. Measurement of the optical density, and thus of the protein complexes present, takes place with a spectrophotometer called a mikrotiter plate reader. The appropriate antibodies required for such a demonstration are commercially available for common proteins. Renaturation of the antigen adsorbed in the first step is proven when a color reaction which was previously absent takes place after treatment with one of the renaturants according to the invention.

The method according to the invention is to be explained further by the following examples, but not restricted in its range of application.

EXAMPLES

Example 1

A $10^{-6}$ M solution of human serum albumin (HSA supplied by SIGMA) in phosphate-buffered solution (supplied by SIGMA) with a pH of 7.4 was prepared, and the CD spectrum of the native human serum albumin depicted in FIG. 1 was recorded. The solution was then heated at 85° C. for 30 min, which denatured the protein. A CD spectrum of the denatured protein solution was then recorded (likewise FIG. 1), and the shape of this curve differs considerably from that of the spectrum for the native protein. Then sufficient trifluoroethanol was added to make its concentration in the aqueous medium 23% by volume. After 10 min, another CD spectrum was recorded (likewise FIG. 1), and the shape of this curve resembles the original spectrum more greatly than that of the denatured HSA, which indicates renaturation.

Confirmation of the regeneration of the biological functions of the albumin by the addition of trifluoroethanol was obtained by assaying with an ELISA. Supports coated with a methyl-terminated silane film (octyltrichlorosilane supplied by Aldrich) were used for this. Three such supports were immersed in a phosphate-buffer solution (supplied by SIGMA) of human serum albumin (supplied by SIGMA) with a pH of 7.4 and a protein concentration of 30 µg/ml for 30 min to adsorb proteins. Two of the supports coated with HSA were heated in pure phosphate buffer at 85° C. for 30 min to denature the proteins. One of these samples was then treated with a 20% strength solution of trifluoroethanol in phosphate buffer for 5 min ELISA measurements were carried out on all three samples, using polyclonal antibodies. The signal intensities obtained thereby are listed in the following table, standardizing to the signal of the native proteins:

| Coating of the support | ELISA signal [%] |
| --- | --- |
| adsorbed albumin native | 100 |
| adsorbed albumin denatured | 73 |
| adsorbed albumin denatured and treated with trifluoroethanol | 77 |

Example 2

Figure 2:
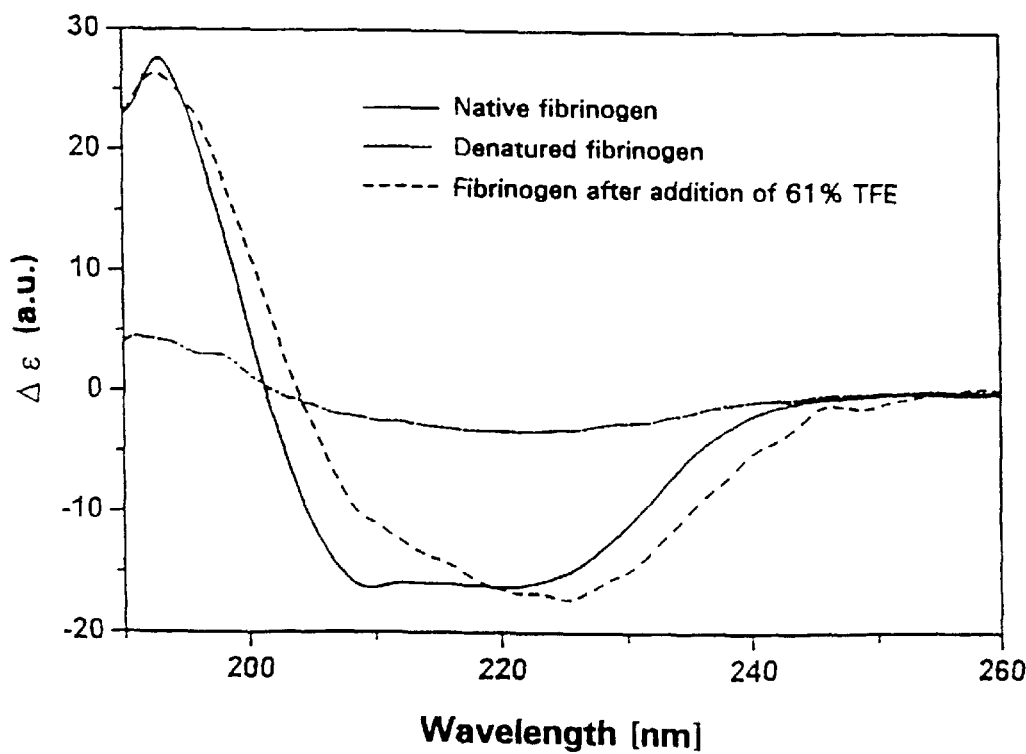

A $10^{-6}$ M solution of human fibrinogen (HFb supplied by SIGMA) in phosphate-buffered solution (supplied by SIGMA) with a pH of 7.4 was prepared, and the CD spectrum of the native HFb depicted in FIG. 2 was recorded. The solution was then heated at 85° C. for 30 min which denatured the protein. A CD spectrum of the denatured protein solution was then recorded (likewise FIG. 2), and the shape of this curve differs considerably from that of the spectrum for the native protein. Then sufficient trifluoroethanol was added to make its concentration in the aqueous medium 61% by volume. After 10 min, another CD spectrum was recorded (likewise FIG. 2), and the shape of this curve resembles the original spectrum more greatly than that of the denatured HFb, which indicates renaturation.

Confirmation of the regeneration of the biological functions of the fibrinogen by the addition of trifluoroethanol was obtained by assaying with an ELISA. Supports coated with a methyl-terminated silane film (octyltrichlorosilane supplied by Aldrich) were used for this. Three such supports were immersed in a phosphate-buffer solution (supplied by SIGMA) of human fibrinogen (supplied by SIGMA) with a pH of 7.4 and a protein concentration of 30 μg/ml for 30 min to adsorb proteins. Two of the supports coated with HFb were heated in pure phosphate buffer at 85° C. for 30 min to denature the proteins. One of these samples was then treated with a 61% strength solution of trifluoroethanol in phosphate buffer for 5 min ELISA measurements were carried out on all three samples, using polygonal antibodies. The signal intensities obtained thereby are listed in the following table, standardizing to the signal of the native proteins:

| Coating of the support | ELISA signal [%] |
| --- | --- |
| adsorbed fibrinogen native | 100 |
| adsorbed fibrinogen denatured | 64.4 |
| adsorbed fibrinogen denatured and treated with trifluoroethanol | 79.2 |

This application is based upon German patent Application No. 197 22 950.6 filed with the German Patent Office on May 31, 1997, the entire contents of which are herein incorporated by reference.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for renaturation of a denatured protein, comprising:

treating a denatured protein which is adsorbed onto a solid support with a renaturant, thereby renaturating said denatured protein to produce a renatured protein, wherein said renaturant is a compound comprising a pair of vicinal carbon atoms, wherein a hydroxyl group is bonded to one vicinal carbon atom, and a fluorine atom is bonded to the other vicinal carbon atom.

2. The method of claim 1, wherein said denatured protein is selected from the group consisting of albumin, fibrinogen, apolipoprotein, lysozyme, subtilisin, ribonuclease, myoglobin, trypsin, chymotrypsin, cytochrome C, calmodulin, melittin, protein C, globulin, histone, prolamin, protamine, keratin, and collagen.

3. The method of claim 1, wherein said renaturant comprises a trifluoromethyl group.

4. The method of claim 1, wherein said renaturant comprises a carboxylic acid group.

5. The method of claim 1, wherein said renaturant comprises an ether linkage.

6. The method of claim 1, wherein said renaturant comprises a plurality of hydrophilic groups.

7. The method of claim 1, wherein said renaturant comprises a plurality of hydroxyl groups.

8. The method of claim 1, wherein said renaturant comprises a plurality of halogen atoms.

9. The method of claim 1, wherein said renaturant comprises a plurality of fluorine atoms.

10. The method of claim 1, wherein said renaturant is soluble in water.

11. The method of claim 1, wherein said renaturant has a solubility of up to 1% by weight in water at 20° C.

12. The method of claim 1, wherein said renaturant is selected from the group consisting of monofluoroethanol, difluoroethanol, trifluoroethanol, 1-fluoro-2-propanol, 1,1-difluoro-2-propanol, 1,1,1-trifluoro-2-propanol, 1,1,1,3-tetrafluoro-2-propanol, 1-trifluoromethyl-1,1-hexanediol, hexafluoroisopropanol, and a mixture thereof.

13. The method of claim 1, wherein said renaturant is trifluoroethanol.

14. The method of claim 1, wherein said denatured protein is renatured while said said support is suspended in a solution.

15. The method of claim 1, wherein said denatured protein is treated at a temperature of from 0° C. to 60° C.

16. The method of claim 1, wherein renaturation is conducted for from 5 to 60 minutes.

* * * * *

UNITED STATES PATENT AND TRADEMARK OFFICE
CERTIFICATE OF CORRECTION

PATENT NO. : 6,022,722

DATED : February 8, 2000

INVENTOR(S): Frauke LOHR, et al.

It is certified that an error appears in the above-identified patent and that said Letters Patent is hereby corrected as shown below:

On the Title page, Item [75], the fifth inventor's residence is incorrect. This should read:

--- [ 75 ] Frauke Lohr, Recklinghausen; Andreas Pawlik, Vechelde; Hubert Motschmann; Martina Bree, both of Berlin, all of Germany; Euridice Vieira, Guimaraes, Portugal; Alexander Welle, Ladenburg, Germany ---

Signed and Sealed this

First Day of May, 2001

Attest:

NICHOLAS P. GODICI

Attesting Officer

Acting Director of the United States Patent and Trademark Office